(12) United States Patent
Olson et al.

(10) Patent No.: US 6,204,009 B1
(45) Date of Patent: Mar. 20, 2001

(54) NUCLEIC ACIDS ENCODING MUTANT RECOMBINANT HEMOGLOBINS CONTAINING HEME POCKET MUTATIONS

(75) Inventors: John S. Olson, Houston, TX (US); Antony J. Mathews, Louisville, CO (US); Jacqueline F. Aitken, Auckland (NZ); Kyoshi Nagai, Cambridge (GB)

(73) Assignee: Baxter Biotech Technology Sàrl, Neuchatâtel (CH)

( * ) Notice: Subject to any disclaimer, the term of this patent is extended or adjusted under 35 U.S.C. 154(b) by 0 days.

(21) Appl. No.: 09/031,361

(22) Filed: Feb. 26, 1998

Related U.S. Application Data (60) Division of application No. 08/381,175, filed on Jan. 30, 1995, which is a continuation-in-part of application No. 08/158,483, filed on Nov. 29, 1993, now Pat. No. 5,449,759, which is a continuation of application No. 07/443,950, filed on Dec. 1, 1989, now abandoned, which is a continuation-in-part of application No. 07/194,338, filed on May 16, 1988, now Pat. No. 5,028,588.

(51) Int. Cl.$^7$ .......................... C12P 21/06; C07K 14/805; C07H 17/00
(52) U.S. Cl. .......................... 435/69.1; 530/385; 536/23.1
(58) Field of Search .......................... 530/385; 536/231; 435/69.1

(56) References Cited

U.S. PATENT DOCUMENTS

| | | | |
|---|---|---|---|
| Re. 34,271 | 6/1993 | Walder | 530/385 |
| 4,826,811 | 5/1989 | Sehgal et al. | 514/6 |
| 5,028,588 | 7/1991 | Hoffman et al. | 514/6 |
| 5,084,558 | 1/1992 | Rausch | 530/385 |
| 5,194,590 | 3/1993 | Sehgal et al. | 530/385 |
| 5,239,061 | 8/1993 | Fronticelli et al. | 530/385 |

FOREIGN PATENT DOCUMENTS

| | | | |
|---|---|---|---|
| 8809179 | 12/1988 | (WO) | |
| 9013645 | 11/1990 | (WO) | |
| 9116349 | 10/1991 | (WO) | |
| 9211283 | 7/1992 | (WO) | |
| 9222646 | 12/1992 | (WO) | |
| 9308831 | 5/1993 | (WO) | |
| 9316721 | 9/1993 | (WO) | |
| 0307087 | 6/1994 | (WO) | |
| 97/04110 | 2/1997 | (WO) | C12N/15/63 |
| 97/15591 | 5/1997 | (WO) | C07K/14/205 |
| 97/23631 | 7/1997 | (WO) | C12N/15/62 |

OTHER PUBLICATIONS

Nagai, K. et al.; "Generation of β–Globin by Sequence–Specific Proteolysis of a Hybrid Protein Produced in *Escherichia coli*"; Nature 309, 810–812 (1984).

Nagai, K. et al.,; "Oxygen Binding Properties of Human Mutant Hemoglobins Synthesized in *Escherichia coli*"; Proc. Natl. Acad. Sci. USA 82, 7252–7255 (1985).

Luisi et al.; "Crystallographic Analysis of Mutant Human Haemoglobins made in *Escherichia coli*"; Nature 320, 555–556 (1986).

Springer et al.; "High–level Expression of Sperm Whale Myoglobin in *Escherichia coli*"; Proc. Natl. Acad. Sci. USA 84, 8961–8965 (Dec. 1987).

Nagai et al.; "Synthesis and Sequence–Specific Proteolysis of Hybrid Proteins produced in *Escherchia coli*"; Methods Enzymol. 153, 461–481 (1987).

Nagai et al.; "Distal Residues in the Oxygen Binding Site of Haemoglobin Studied by Protein Engineering"; Nature 329, 858–860 (1987).

Olson et al.; "The Role of the Distal Histidine in Myoglobin and Haemoglobin"; Nature 336, 265–266 (1988).

Matthews et al.; "The Effects of E7 and E11 Mutations on the Kinetics of Ligand Binding to R State Human Hemoglobin*"; J. Biol. Chem. 264, 16573–16583 (1989).

Egeberg et al.; "The Role of Val$^{68}$ (E11) in Ligand Binding to Sperm Whale Myoglobin"; J. Biol. Chem. 265, 11788–11795 (1990).

Rohlfs et al.; "The Effects of Amino Acid Substitution at Position E7 (Residue 64) on the Kinetics of Ligand Binding to Sperm Whale Myoglobin*"; J. Biol. Chem. 265, 3168–3176 (1990).

Tame et al.; "Functional Role of the Distal Valine (E11) Residue of α Subunits in Human Haemoglobin"; J. Mol. Biol. 218, 761–767 (1991).

Fronticelli & Shoaee Modulation of Nitric Oxide Affinity By Amino Acid Resides in the Pocket of the B–Chains/Art. Cells, Blood Subs & Immobi. Biotech./(1994) 22(5);83.

Militello Et Al/Dynamic Properties of Some β–Chain Mutant Hemoglobins/Proteins: Struc–ture, Function, and Genetics/(1995) 22:12–19.

Fronticelli Et Al./Recombinant Human Hemoglobin: Modification of the Polarity of the β–Heme Pocket by a Valine$^{67}$ (E11)→Threonine Mutation/Biochemistry/(1993) 32:1235–1242.

Doherty et al., Rate of Reaction with Nitric Oxide Determines the Hypertensive Effect of Cell–Free Hemoglobin, Nature Biotechnology, vol. 16, Jul. 1998, pp. 672–676.

Weickert et al., Turnover of Recombinant Human Hemoglobin in *Escherichia coli*Occurs Rapidly for Insoluble and Slowly for Soluble Globin, Archives of Biochemistry and Biophysics, vol. 348, No. 2, Dec. 15, 1997, pp. 337–346.

(List continued on next page.)

*Primary Examiner*—Karen Cochrane Carlson
(74) *Attorney, Agent, or Firm*—Senniger, Powers, Leavitt & Roedel

(57) ABSTRACT

This invention relates to recombinant hemoglobins containing mutations in or near the heme pocket of the hemoglobin molecule. This invention particularly relates to recombinant hemoglobins that have altered geometry or polarity around the distal portion of the heme pocket.

24 Claims, 3 Drawing Sheets

OTHER PUBLICATIONS

Eich et al., Mechanism of NO–Induced Oxidation of Myoglobin and Hemoblobin, 1996 American Chemical Society, Biochemistry 1996, vol. 35, No. 22, pp. 6976–6983.

Shen et al., Production of Unmodified Human Adult Hemoglobin *Escherichia coli,* Proc. Natl. Acad. Sci., vol. 90, Sep. 1993, pp. 8108–8112.

Dumoulin et al., Two Mutations in Recombinant Hb β F41 (C7) Y, K82 (EF6)D Show Additive Effects in Decreasing Oxygne Affinity Protein Science 1996, pp. 114–120.

Pechik et al., Crystallographic, Molecular Modeling, and Biophysical Characterization of the Valineβ67 (E11) Threonine Variant of Hemoglobin, Biochemistry 1996, vol. 35, No. 6, pp. 1935–1945.

Kiger et al., Recombinant [Pheβ63]Hemoglobin Shows Rapid Oxidation of the β Chains and Low–Affinity, Non–Cooperative Oxygen Binding to the α Subunits, Eur. J. Biochem. 243, Feg. 1997, pp. 365–373.

Hoffman et al., Expression of Fully Functional Tetrameric Human Hemoglobin in *Escherichia coli,* Proc. Natl. Acad. Sci., vol. 87, Nov. 1990, pp. 8521–8525.

Ogata Et Al/Hemoglobin Sendagi (β42 PHE→VAL): A New Unstable Hemoglobin Variant Having an Amino Acid Subsitution At CD1 of the β–Chain/Hemoglobin, 10(5): 469–481 (1986).

Wajcman Et Al/Two New Hemoglobin Variants with Deletion Hemoglobin Tours . . . Biochimica Et Biophysica Acta, 295: 495–504 (1973).

Rachmilewitz, E.A./Denaturation of the Normal and Abnormal Hemolgobin Molecules/Seminars in Hematology/ (1974) 11(4): 441–462.

Reichelt, H. Et Al/Blood Substitutes Made on the Basis of Perfluorocarbons Inhibit Intracellular Energy Generation/ Blood Substitutes and Oxygen Carriers/(1992) 769–772/ T.M. Chaing Editor.

Spahn, D.R. Et Al/Cardiovascular and Coronary Physiology of Acute Isovolemic Hemodilution: A Review of Nonoxygen–Carrying and Oxygen–Carrying Solutions/Anesth Analg/(1994) 78:1000–1021.

Springer, B.A. Et Al/Chemical Rev./Mechanisms of Ligand Recognition in Myoglobin/(1994) 94: 699–714.

Vlahakes, G.J. Et Al/Hemodynamic Effects and Oxygen Transport Properties of a New Blood Substitute in a Model of Massive Blood Replacement/J. Thorac Cardiovasc. Surg/ (1990) 100: 379–388.

White, C.T. Et Al/Toxicity of Human Hemoglobin Solution Infused Into Rabbits/J. Lab Clin Med/(1986) 108: 121–131.

Biro, G.P. Et Al/Studies on Blood Substitutes Based On Hemoglobin and Perfluorocarbon/ Biomat., Art. Cells & Immob. Biotech./(1992) 20(2–4): 1013–1020.

Winslow, R.M./Hemoglobin–Based REd Cell Substitutes/ (1992) Entire Book/The Johns Hopkins Univ. Press/Baltimore.

Snyder, S.H. & Bredt, D.S./Biological Roles of Nitric Oxide/Scientific American/(1992) May 68–77.

Fermi, G. Et Al/The Crystal Structure of Human Deoxyhaemoglobin At 1–74 A Resolution/ J. Mol. Biol./(1984) 175: 159–174.

Looker, D. Et Al/Expression of Recombinant Human Hemoglobin in *Escherichia coli*/ Methods in Enzymology/(1994) 231:364–374.

Mathews, A.J. Et Al/The Effects of E7 and E11 Mutations on the Kinetics of Ligand Binding To R State Human Hemoglobin/J. of Biol. Chem./(1989) 264(28):16573–16583.

Moncada, S. Et Al/Nitric Oxide: Physiology, Pathophysiology and Pharmacology/ Pharm. Reviews/(1991) 43(2): 109–142.

Perutz, M.F./Myoglobin and Haemoglobin: Role of Distal Residues in Reactions With Heam Lignads/Trends Biochem. Sci./(1989) 14:42–44.

NUCLEIC ACIDS ENCODING MUTANT RECOMBINANT HEMOGLOBINS CONTAINING HEME POCKET MUTATIONS

This application is a divisional of U.S. Ser. No. 08/381,175 filed on Jan. 30, 1995 which is a CIP of U.S. Ser. No. 08/158,483 filed on Nov. 29, 1993, issued as U.S. Pat. No. 5,449,759, which is a Continuation of U.S. Ser. No. 07/443,950 filed on Dec. 1, 1989, now abandoned, which is a CIP of U.S. Ser. No. 07/194,338, filed May 16, 1988, issued as U.S. Pat. No. 5,028,588.

FIELD OF THE INVENTION

This invention relates to mutant recombinant hemoglobins containing mutations around one or more of the heme pockets of the hemoglobin molecule. The invention relates particularly to mutant recombinant hemoglobins that have altered geometry or polarity around the distal portion of the heme pocket which results in mutant recombinant hemoglobins with reduced autooxidation rates, reduced or increased affinities for ligands or both reduced autooxidation and changed ligand affinity.

BACKGROUND OF THE INVENTION

Loss of blood often requires replacement of both the volume of fluid that is lost and the oxygen carrying capacity of that fluid This is typically accomplished by transfusing red blood cells, either as packed RBC's or as units of whole blood. However, it is not always possible, practical or desirable to transfuse a patient with donated blood. Human blood transfusions are associated with many risks and limitations, such as:

1) Infectious disease transmission (i.e., human immunodeficiency virus (HIV), non-A and non-B hepatitis, hepatitis B, *Yersinia enterocolitica*, cytomegalovirus, human T-cell leukemia virus 1)
2) Immunologic reaction (i.e., hemolytic transfusion reaction, immunosuppresion, graft versus host reaction)
3) Typing and cross-matching required prior to administration
4) Limited availability
5) Limited stability (shelf life of 42 days or less; cannot be frozen)

When human blood is not available or the risk of transfusion is too great, volume can be replaced utilizing plasma expanders such as colloid and crystalloid solutions but to date, none of the volume replacement therapies currently approved for human use can transport oxygen. In situations where replacement of lost blood is necessary and blood is not available for transfusion, a red blood cell substitute that can transport oxygen, such as a hemoglobin solution, is desirable. Administration of a hemoglobin solution can increase and/or maintain plasma volume and decrease blood viscosity in the same manner as conventional plasma expanders, but, in addition, a hemoglobin-based red blood cell substitute should be able to support adequate transport of oxygen from the lungs to peripheral tissues. Moreover, an oxygen-transporting hemoglobin-based solution may be used in most situations where red blood cells are currently utlized. For example, oxygen-transporting hemoglobin-based solution may be used to temporarily augment oxygen delivery during or after pre-donation of autologous blood prior to the return of the autologous blood to the patient.

To address this need, a number of red cell substitutes have been developed (Winslow, R. M.(1992) *Hemoglobin-based Red Cell Substitutes*, The Johns Hopkins University Press, Baltimore 242 pp). These substitutes include synthetic perfluorocarbon solutions, (Long, D. M. European Patent 0307087), stroma-free hemoglobin solutions, both chemically crosslinked and uncrosslinked, derived from a variety of mammalian red blood cells (Rausch, C. and Feola, M., U.S. Pat. Nos. 5,084,558 and 5,296,465; Sehgal, L. R., U.S. Pat. Nos. 4,826,811 and 5,194,590; Vlahakes, G. J. et al., (1990) J. Thorac. Cardiovas. Surg. 100: 379–388) and hemoglobins expressed in and purified from genetically engineered organisms (for example, non-erytocyte cells such as bacteria and yeast, Hoffman et al., WO 90/13645; bacteria, Fronticelli, C. et al., U.S. Pat. No. 5,239,061; yeast, De Angelo et al., WO 93/08831 and WO 91/16349; and transgenic mammals, Logan et al., WO 92/22646; Townes, T. M and McCune, S. L., WO 92/11283). These red blood cell substitutes have been designed to replace or augment the volume and the oxygen carrying capability of red blood cells.

The oxygen carrying portion of the red blood cell is the protein hemoglobin. Hemoglobin is a tetrameric protein molecule composed of two identical alpha globin subunits ($\alpha_1$, $\alpha_2$), two identical beta globin subunits ($\beta_1$, $\beta_2$) and four heme molecules. A heme molecule is incorporated into each of the alpha and beta globins to give alpha and beta subunits. Heme is a large macrocyclic organic molecule containing an iron atom; each heme can combine reversibly with one ligand molecule such as oxygen. In a hemoglobin tetramer, each alpha subunit is associated with a beta subunit to form two stable alpha/beta dimers, which in turn associate to form the tetramer (a homodimer). The subunits are noncovalently associated through Van der Waals forces, hydrogen bonds and salt bridges.

In the unliganded state (deoxygenated or "deoxy") state, the four subunits form a quaternary structure known as "T" (for "tense") state. During ligand binding, the $\alpha_1\beta_1$ and $\alpha_1\beta_1$ and $\alpha_2\beta_2$ interfaces remain relatively fixed while the $\alpha_1\beta_2$ and $\alpha_2\beta_1$ interfaces exhibit considerable movement. When a ligand is bound to the hemoglobin molecule, the intersubunit distances are increased relative to the deoxygenated distances, and the molecule assumes the "relaxed" or "R" quaternary structure which is the thermodynamically stable form of the molecule when three or more ligands are bound to the heme.

Red blood cell replacement solutions have been administered to animals and humans and have exhibited certain adverse events upon administration. These adverse reactions may include hypertension due to vasoconstriction, renal failure, neurotoxicity, and liver toxicity (Winslow, R. M., ibid., Biro, G. P. et al., (1992) Biomat., Art. Cells & Immob. Biotech. 20: 1013–1020) and in the case of perfluorocarbons, hypertension, activation of the reticuloendothelial system and complement activation (Reichelt, H. et al., (1992) in Blood Substitutes and Oxygen Carriers, T. M. Chang (ed.), pg. 769–772; Bentley, P. K. ibid, pp. 778–781). For hemoglobin based oxygen carriers, renal failure and renal toxicity is the result of the formation of hemoglobin $\alpha/\beta$ dimers. The formation of dimers can be prevented by chemically crosslinkng (Sehgal, et al, U.S. Pat. Nos. 4,826,811 and 5,194,590; Walder, J. A. U.S. Reissue Pat. No. RE34271) or genetically linking (Hoffman, et al., WO 90/13645) the hemoglobin dimers so that the tetramer is prevented from dissociating.

However, prevention of dimer formation has not alleviated all of the adverse events associated with hemoglobin administration. Blood pressure changes upon administration of hemoglobin solutions have been attributed to vasoconstriction resulting from the binding of endothelium derived relaxing factor (EDRF) by hemoglobin (Spahn, D. R. et al., (1994) Anesth. Analg. 78: 1000–1021; Biro, G. P., (1992) Biomat., Art. Cells & Immob. Biotech., 20: 1013–1020; Vandegriff, K. D. (1992) *Biotechnology and Genetic Engineering Reviews,* Volume 10: 404–453 M. P. Tombs, Editor, Intercept Ltd., Andover, England). Endothelium derived relaxing factor has been identified as nitric oxide (NO) (Moncada, S. et al., (1991) Pharmacol. Rev. 43: 109–142 for review); both inducible and constitutive NO are primarily produced in the endothelium of the vasculature and act as local modulators of vascular tone. CO has also been implicated in blood pressure regulation since it can also activate guanylate cyclase (Snyder, S. H. and Bredt, D. S. (1992) Sci. American May, 68–77). Hemoglobin can bind both nitric oxide and carbon monoxide, thus preventing vascular relaxation and potentially leading to the hypertension sometimes observed upon administration of extracellular hemoglobin solutions. In addition to direct binding to deoxyhemoglobin, NO can also oxidize oxyhemoglobin producing peroxynitrite and methemoglobin. This reaction could also lower free concentrations of NO and lead to hypertension.

Some inflammatory responses are also mediated by nitric oxide (Vandegriff, ibid., Moncada, S., et al., ibid.). For example, nitric oxide produced by the endothelium inhibits platelet aggregation and as nitric oxide is bound by cell-free hemoglobin solutions, platelet aggregation may be increased. As platelets aggregate, they release potent vasoconstrictor compounds such as thromboxane $A_2$ and serotonin (Shuman, M. (1992) *in Cecil Textbook of Medicine,* J. B. Wyngaarden, L. H. Smith and J. C. Bennett, ed., W. B. Saunders Co, Philadelphia, pages 987–992). These may act synergistically with the reduced nitric oxide levels due to binding by hemoglobin to result in an exaggerated vasoconstriction.

In addition to modulating platelet aggregation, nitric oxide inhibits neutrophil attachment to cell walls. Increased adhesion of neutrophils to cell walls may lead to cell wall damage. Endothelial cell wall damage has been observed upon infusion of some hemoglobin solutions; this kind of damage is consistent with uptake of endogenous nitric oxide by hemoglobin (White, et al., (1986) J. Lab. Clin. Med. 108: 121–131; Vandegriff (1992) ibid). In all these cases, a hemoglobin molecule with reduced reactivity for either binding or oxidizing nitric oxide and with a physiologically acceptable oxygen affinity might ameliorate some of these observed adverse events while still functioning as an effective oxygen carrier.

Conversely, while a moderate production of nitric oxide is required to maintain appropriate vascular tone, excess production of nitric oxide by the endothelium and other nitric oxide producing cells, such as macrophages, may result in pathological states. These disease states include septic shock and nitric oxide mediated hypotension. In these cases, binding of excess nitric oxide or its oxidation by a hemoglobin with a particularly high reactivity for nitric oxide may be useful (Kilbourn, PCT Application Number WO 93/16721).

Another disadvantage of hemoglobin-based blood substitutes has been the tendency of the iron in the heme to undergo oxidation. The oxidation of the iron in the heme from the ferrous ($Fe^{+2}$) to the ferric form ($Fe^{+3}$) results in the formation of methemoglobin. Methemoglobin is a non-functional form of hemoglobin that cannot bind oxygen, thus its formation in hemoglobin solutions results in reduced capacity to bind gases and may thus require administration of larger amounts of solution to accomplish the same desired benefit or result In addition, methemoglobin molecules are vulnerable to accelerated degradation due to hemichrome formation, heme loss, precipitation, and reaction with hydrogen peroxide to form toxic radicals and the like (Bunn, H. F. and Forget, B. G. *Hemoglobin: Molecular, Genetic and Clinical Aspects,* W. B. Saunders Company, Philadelphia, 690 pp, hereby incorporated by reference; Rachmilewitz, E. A. (1974) Sem. Hematol. 11: 441–462).

Myoglobin is a monomeric heme protein found in muscle which binds oxygen reversibly which has often been used as a simple model for the complex chemistry of tetrameric hemoglobin. Myoglobin appears to be an adequate model for ligand binding to the alpha subunits of hemoglobin. In contrast, it is a less satisfactory model for the ligand binding and oxidative behavior of the beta subunit. Moreover, because myoglobin is a non-cooperative molecule, changes in overall ligand affinity and oxidation are not predictable when a mutation in myoglobin is transferred to the equivalent location in the hemoglobin molecule.

Figure 1A:
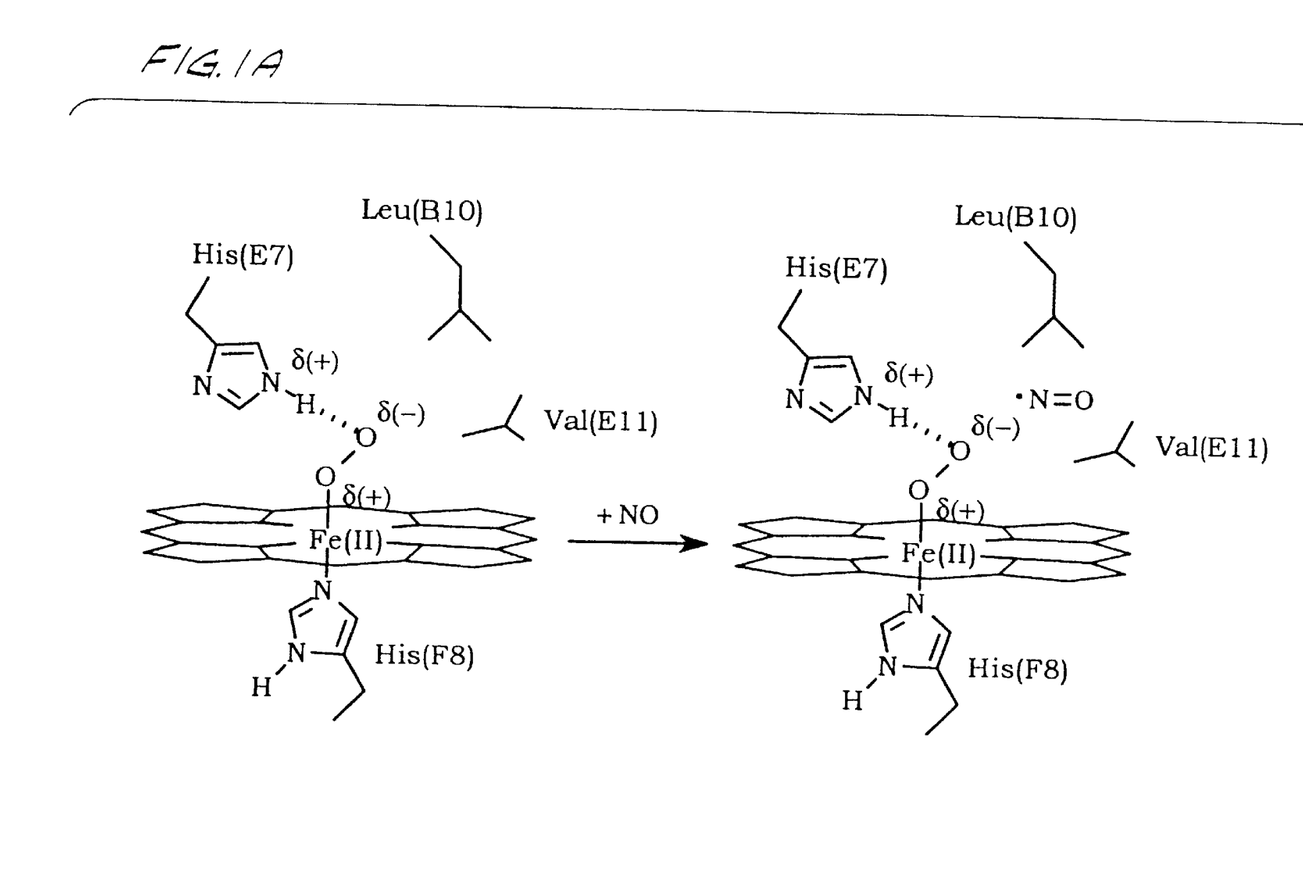
FIGS. 1A and 1B shows the proposed mechanism for the reaction of NO with oxyhemoglobin.
Figure 1B:
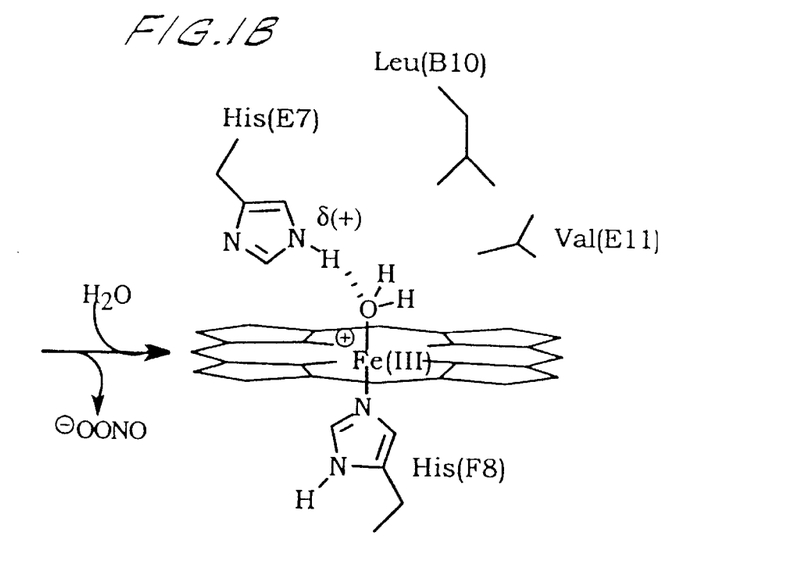

Nevertheless, the autooxidation rate and the discrimination between $O_2$, CO, and NO in both myoglobin and hemoglobin appear to be the result of polar interactions between bound ligands and the histidine found at the E7 position in both proteins. In unliganded myoglobin and the subunits of hemoglobin, a $H_2O$ molecule is hydrogen bonded to the histidine and must be displaced before a ligand can bind to the iron atom of the heme. The binding of all three ligands requires displacement of this water molecule. In the case of $O_1$ binding, the inhibition caused by the displacement of the water molecule is overcome by much more favorable hydrogen bonding interactions between His-E7 and the polar $Fe^{\delta(+)}$—O—$O^{\delta(-)}$ complex. No favorable interactions occur between bound CO and the histidine at the E7 position. Thus the affinity of hemoglobin for CO is primarily a function of the intrinsic strength of the covalent bond between CO and the heme iron atom, and as a result, the requirement for $H_2O$ displacement results in a net inhibition of CO binding. Without this inhibition, CO would bind approximately 10 fold more tightly to alpha subunits of hemoglobin, and the discrimination against it and for oxygen would be compromised. NO binding shows an intermediate situation; the inhibition due to water displacement is exactly balanced by a weak hydrogen bond with His-E7. As a result, the NO affinity of hemoglobin is similar to that of model heme compounds. Note also that the formation of the iron-oxygen/His E7 complex results in both a net enhancement of oxygen affinity relative to carbon monoxide affinity and a decrease in spontaneous iron oxidation. Thus oxygen affinity and autooxidation are often tightly coupled. In addition, oxidation can occur by an NO mediated mechanism (FIGS. 1A and 1B). NO is a free radical and can react rapidly with reduced iron-oxygen complexes to form peroxynitrite (—OONO) and ferric iron. In hemoglobins and myoglobins, the NO must first diffuse into the heme pocket and take a position in cavity circumscribed by Val(E11), Leu(B10), Phe(CD1), and Leu or Ile(G8) after which reaction with the bound oxygen occurs. Placement of large aromatic residues at these positions should inhibit this oxidative process and prevent NO consumption by oxyhemoglobin.

An effective extracellular hemoglobin blood substitute must bind oxygen cooperatively with moderately low affinity ($P_{50} \geq 20$–30 mm Hg or 30 to 50 $\mu$M free $O_2$ measured at 37° C.): where the $P_{50}$ defined as the oxygen partial pressure at half saturation of hemoglobin) and must have large association and dissociation rate constants for oxygen binding to allow efficient uptake in the lungs and delivery in muscle capillaries. The rate and extent of oxygen delivery is proportional to the $P_{50}$ of the extracellular hemoglobin or red cells present in muscle capillaries (Vandegriff, K. D., and Olson, J. S. (1984) J. Biol. Chem. 259: 12619–12627.; Lemon, D. et al., (1987) J. Appl. Physiol. 62: 798–806; Nair, P.K. et al., (1989) Microvascular Research 38: 269–285). Lowering oxygen affinity results in more efficient $O_2$ transport and is limited only by the need to achieve 80–90% saturation in the alveolar capillaries. Unfortunately, almost all attempts to raise $P_{50}$ by chemical modification, mutation, and allosteric effectors cause higher rates of autooxidation and subsequent hemin loss and denaturation. Brantley et al. (Brantley, R. E. Jr., et al., (1993) J. Biol. Chem. 268: 6995–7010) have shown that there is strong inverse correlation between oxygen affinity and the rate of autooxidation, $k_{ox}$, for 27 different recombinant myoglobins. Similar correlations have been noted both anecdotally and experimentally for tetrameric hemoglobins (Vandegriff, K. D. (1992) Biotechnology and Genetic Engineering Reviews 10: 403–453). This is a major stumbling block for engineering more efficient blood substitutes since stability is compromised by elevated $P_{50}$ values.

The dominant mechanism for autooxidation in myoglobin, and quite likely hemoglobin, involves protonation of the Fe(II)0246—$O_2$ complex and dismutation into Fe(III) and the neutral perhydroxyl radical $HO_2$. The bimolecular reaction of molecular $O_2$ with deoxymyoglobin containing weakly coordinated water only contributes to the observed rate when the unimolecular Fe(II)—O—O—$H^{(+)}$ dissociation process is slow, and then only when the $O_2$ concentration approaches the $P_{50}$. In native oxymyoglobin, the neutral side chain of His(E7) forms a hydrogen bond with the bound ligand. This interaction increases $O_2$ affinity and, at the same time, decreases the rate of autooxidation, by preventing net protonation of the Fe—$O_2$ complex since the $pK_a$ for forming the imidazolate anion is $\geq 12$.

Based on the physical-chemical mechanisms underlying spontaneous and NO induced autooxidation of the heme in the distal pocket and the binding of ligands at the heme group, the inventors have redesigned the active site in the region directly adjacent to the heme iron atom to moderate both the oxidation rate and ligand affinity. The present inventors have been able to develop strategies for selectively altering the specificity of recombinant heme proteins for the three physiologically important gases, $O_2$, CO, and NO, and for decoupling the rate of oxidation of the iron atom from affinity for gaseous ligands. The present inventors have discovered that if the distal residue histidine at position E7 of either the alpha or the beta globin is replaced with certain other amino acids, the affinity of the resultant hemoglobin mutant for both NO and CO can be increased Likewise, replacement of leucine at the B10 helical position of the alpha or beta globin can result in a hemoglobin that shows high affinity for NO without a concomittant increase in affinity for CO. In addition, the inventors have also discovered that there are mutations of the distal heme pocket that inhibit dramatically the reactions of NO and CO with hemoglobin. These mutations include replacements of Leu-B 10, Val-E11, and His-E7, and various multiple combinations of these mutations, particularly double and triple combinations. Lastly, the present inventors have discovered that to protect against protonation by solvent water and subsequent oxidation of the iron, the spaces adjacent to the bound oxygen can be filled with large aromatic residues. These aromatic groups exclude water by their steric effects and partially stabilize the polar iron-oxygen complex by interactions between the phenyl ring electronic multipole and bound oxygen. The size (the free volume) of the distal pocket can be decreased by introducing these and As other mutations, and this decrease in size of the distal pocket also excludes other exogenous oxidizing agents such as NO and $H_2O_2$ from direct reaction with bound $O_2$ (FIGS. 1A and 1B).

Genetic engineering techniques have allowed the expression of heterologous proteins in a number of biological expression systems, such as insect cells, plant cells, transgenic cells, yeast systems and bacterial systems. Because the sequences of alpha and beta globin of hemoglobin are known, and efficient expression criteria have been determined, it is possible that any suitable biological protein expression system can be utilized to produce large quantities of mutant recombinant hemoglobin. Indeed, hemoglobin has been expressed in a number of biological systems, including bacteria (Hoffman et al., WO 90/13645), yeast (De Angelo et al., WO 93/08831 and WO 91/16349; Hoffman et al., WO 90/13645) and transgenic mammals (Logan et al., WO 92/22646; Townes, T. M and McCune, S. L., WO 92/11283).

Mutants of hemoglobin are known and disclosed in PCT publication number W088/09179, hereby incorporated by reference. Brief reviews of the effects of some distal pocket mutations on ligand binding to myoglobin and hemoglobin have been presented by Perutz (Perutz, M. F. (1989) Trends Biochem. Sci. 14: 42–44); Springer et al. (Springer, B. A., et al (1994) Chem. Rev. 94: 699–714) and Mathews et al. (Mathews, A. J. et al., (1989) J. Biol. Chem. 264: 16573–16583) and the differences between myoglobin and hemoglobin have been noted in these and other publications. Both the alpha and beta globin subunits have been sequenced (Hoffman and Nagai, U.S. Pat. No. 5,028,588, hereby incorporated by reference) and techniques for the mutation, expression and purification of the mutant recombinant hemoglobins have been described (Looker, D. et al. (1994) *Expression of Recombinant Hemoglobin in Escherichia coli* In: Methods in Enzymology 231: 364–374, S. O. Colowick, ed.; Academic Press, Inc.; Hoffman et al., WO 93/13645; Milne et al., co-pending U.S. application Ser. No. 08/339,304, filed Nov. 14, 1994).

SUMMARY OF THE INVENTION

This invention relates to mutant recombinant hemoglobins containing mutations in or near the heme pocket of the hemoglobin molecule. More particularly, this invention relates to mutant recombinant hemoglobins that have altered geometry or polarity around the distal portion of the heme pocket.

Further, the present invention relates to mutant recombinant hemoglobin molecules containing heme pocket mutations wherein the mutations result in a mutant recombinant hemoglobin having autooxidation rates lower than autooxidation rates measured for naturally occurring purified human hemoglobin under comparable conditions. Representative examples of mutations that result in such reduced autooxidation rate hemoglobin mutants include:

Leu-B10→Phe
Val-E11→Phe
both His-E7→Gln and Val-E11→Phe
both His-E7→Gln and Leu-B10→Phe
His-E7→Gln, Leu-B10→Phe and Val-E11→Phe and
His-E7→Phe, Leu-B10→Phe and Val-E11→Phe.

The present invention also relates to mutant recombinant hemoglobin molecules containing heme pocket mutations wherein the mutations result in a mutant recombinant hemoglobin having an affinity for gaseous ligands greater than or less than purified natural human hemoglobin measured under the same conditions. Preferably, the gaseous ligands bind to the hemoglobin at the heme pocket of the hemoglobin molecule and more preferably, the gaseous ligands are selected from the group consisting of carbon monoxide and nitric oxide, most preferably the gaseous ligand is nitric oxide. The mutant recombinant hemoglobin molecules of the present invention preferably contain mutations that result in alteration of the amino acid composition of distal pocket so that the distal pocket amino acid composition no longer matches the amino acid composition of human hemoglobin. Representative examples of mutations that result in mutant recombinant hemoglobins with altered affinity for gaseous ligands include the following site specific mutations:

Leu-B10→Trp
Leu-B10→Phe
Leu-B10→Val
Leu-B10→Ile
Leu-B10→Ala
His-E7→Leu
His-E7→Trp and
Val-E11→Phe
Val-E11→Trp It is also within the scope of this invention to provide methods for the preparation of mutant recombinant hemoglobins with altered affinities and/or oxidation properties by appropriate mutation of the alpha and/or beta globin gene, expression and purification of the mutant recombinant hemoglobin. Methods for selecting candidate mutations and evaluating their ligand affinities are described herein. The invention is further directed to mutant recombinant hemoglobins containing the above described mutations in the alpha subunit, the beta subunit, or both the alpha and beta subunits and having altered autooxidation or affinity for gaseous ligands, preferably having altered affinity for nitric oxide or carbon monoxide. The invention further relates to DNA's or vectors containing DNA sequences coding for the mutant recombinant hemoglobins of the invention.

The invention further relates to pharmaceutical compositions containing the mutant recombinant hemoglobins of the invention.

Specific embodiments of the present invention include hemoglobins with both unusually high and low affinities for carbon monoxide or nitric oxide. In another embodiment of the invention, hemoglobins are provided which are recombinant oxyhemoglobins with reduced affinity for NO and decreased NO and $H_2O_2$ mediated oxidation relative to naturally occurring human hemoglobins.

Other features and advantages of the invention will be apparent from the following description of the preferred embodiments thereof and from the claims.

Unless defined otherwise, all technical and scientific terms used herein have the same meaning as commonly understood by one of ordinary skill in the art. Although any methods and materials similar or equivalent to those described herein can be used in the practice or testing of the present invention, the preferred methods and materials are now described. Unless mentioned otherwise, the techniques employed or contemplated herein are standard methodologies well known to one of ordinary skill in the art For the purposes of this invention, "naturally occurring human hemoglobin", "native hemoglobin" or "conventional hemoglobin" refer to the species of hemoglobin A whose alpha and beta chains amino acid sequences are the same as the amino acid sequences given in SEQ ID.:1 AND SEQ ID.:2, respectively. Note that it is conventional to identify the helical segments of the globin subunits by letters, for example, the proximal histidine of the alpha chain or the beta chain is termed F8 (residue 8 of helix F). The non-helical segments are identified by letter pairs, indicating which helical segments they connect, for example, non-helical segment BC connects helix B and helix C. The helical notation and corresponding amino acids for alpha and beta globin are shown in Table 1.

"Recombinant hemoglobin" means hemoglobin, whether native or mutant, comprising alpha-like globin proteins and/or beta-like globin proteins, at least one of which is obtained by expression of a globin gene carried by a recombinant DNA molecule in a cell other than the cell in which that hemoglobin gene and/or hemoglobin protein is naturally found, i.e., the hemoglobin gene is heterologous to the host in which it is expressed. Therefore, the expression of any human hemoglobin gene in any cell other than a human red blood cell would be considered to be a recombinant hemoglobin. Moreover, the expression of a vertebrate hemoglobin in any species of invertebrate, or any vertebrate other than the vertebrate where the hemoglobin to be expressed is naturally occurring, would be considered a recombinant hemoglobin. The expression of any naturally occurring hemoglobin mutant in any species other than the species in which it is naturally occurring, would be considered a recombinant hemoglobin. The expression of any non-naturally occurring mutant hemoglobin in any species would be considered a recombinant hemoglobin. The expression of a naturally occurring mutant hemoglobin in any individual organism, regardless of species, other than the individual organism in which said mutant is naturally expressed would be considered a recombinant hemoglobin.

An "alpha-like globin" (or domains thereof) has at least about 75% sequence identity with native human alpha globin. However, a polypeptide of lesser sequence identity may still be considered substantially homologous with alpha globin, and thus may be an alpha-like globin, if it has a greater sequence identity than would be expected from chance and also has the characteristic higher structure of alpha globin and similar biological activity. Likewise, a "beta-like globin" (or domains thereof) has at least about 75% sequence identity with native human beta globin. However, a polypeptide of lesser sequence identity may still be considered substantially homologous with beta globin, and thus may be a beta-like globin, if it has a greater sequence identity than would be expected from chance and also has the characteristic higher structure of beta globin and similar biological activity.

"Liganded hemoglobin" means hemoglobin to which a ligand is bound at the heme groups. Common preferred ligands include, but are not limited to $O_2$, CO, NO and the like.

"Oxyhemoglobin" means hemoglobin in which each of the functional oxygen binding sites has bound to it an oxygen molecule.

"Deoxyhemoglobin" or "unliganded hemoglobin" means any hemoglobin to which no ligand is bound to the alpha globin, the beta globin, and/or any functional heme prosthetic group.

"Methemoglobin" or "oxidized hemoglobin" means any hemoglobin in which the iron has been oxidized to the ferric state.

"R-state hemoglobin" is the high affinity state of hemoglobin and is the dominant form of hemoglobin when a ligand is bound at the heme pockets. The ligand is typically oxygen, thus this state is known as the "oxy" or "R" (for relaxed) state. In the R state, intersubunit distances are increased relative to the distances in T-state hemoglobin. "T-state hemoglobin" is the low affinity state of hemoglobin and is the dominant form of hemoglobin when it is deoxygenated ("deoxy", or "T" for "tense").

"Heme pocket" means that pocket formed around the heme of each globin subunit described by the residues and is meant to include residues within about 6 Å of the heme pocket.

"Distal heme pocket" means that portion of the heme pocket above the plane of the heme that contains the free coordination site of the iron where ligand molecules can combine reversibly with the iron atom and which contains such residues as histidine E7 and valine E11. Likewise, the proximal side of the heme pocket is described by those residues below the plane of the heme and contains such residues as the proximal histidine at position F8.

"Oxidation" means the oxidation of the iron in the heme of any or all of the subunits making up the hemoglobin tetramer from the ferrous ($Fe^{+2}$) to the ferric form ($Fe^{+3}$). Autooxidation occurs spontaneously without the addition of exogenous oxidants, however oxidation can be induced by the presence of exogenous oxidizing agents, most notably NO and hydrogen peroxide.

"Mutations" are substitutions, deletions or additions of one or more amino acids to the amino acid sequence that constitutes naturally occurring human hemoglobin.

"Affinity" is the overall binding of a ligand to hemoglobin, and is described by the thermodynamic equilibrium constant, Keq. Affinity is the ratio of the ligand association rate and the hemoglobin—ligand dissociation rate constants, and thus changes in either rate constants can lead to changes in ligand affinity.

"Altered affinity" means the affinity of a recombinant hemoglobin for a gaseous ligand that is at least 10% different from the affinity of naturally occurring human hemoglobin for that same gaseous ligand under the same measurement conditions.

DETAILED DESCRIPTION OF THE INVENTION

This invention relates to mutant recombinant hemoglobins containing mutations around the heme pocket of one or more of the globin subunits. Heme is the prosthetic group of hemoglobin, myoglobin, catalase, peroxidase, and cytochrome b. The heme is inserted in a cleft between the E and F helices. The heme iron is linked covalently to the imidazole nitrogen of the "proximal" F8 histidine. The distal E7 histidine and E11 valine appear to guard the access of oxygen to the heme pocket. The residues of the heme pocket include those residues that are on a nearest atom-to-nearest atom basis within 6 angstroms of the heme moiety, more preferable within 4 angstroms of the heme moiety (Fermi, et al. (1984) J. Mol. Biol. 175: 159–174). These residues include for alpha globins:

| First shell | Second Shell |
|---|---|
| Distal residues: | |
| B10 Leu | B13 Met |
| CE1 Phe | CE3 His |
| E7 His | CE4 Phe |
| E11 Val | E10 Lys |
| G8 Leu | E14 Ala |
| | G12 Leu |
| Proximal residues: | |
| F8 His | C7 Tyr |
| | F4 Leu |
| | F7 Leu |
| | FG3 Leu |
| | FG5 Val |
| | G4 Asn |
| | G5 Phe |
| | H15 Val |
| | H19 Leu | and for beta globin:

| First shell | Second Shell |
|---|---|
| Distal residues: | |
| B10 Leu | B13 Leu |
| CD1 Phe | CD3 Ser |
| E7 His | CD4 Phe |
| E11 Val | E10 Lys |
| G8 Leu | E14 Ala |
| | G12 Leu |
| Proximal residues: | |
| F8 His | C7 Phe |
| | F4 Leu |
| | F7 Leu |
| | FG3 Leu |
| | FG5 Val |
| | G4 Asn |
| | G5 Phe |
| | G12 Leu |
| | H15 Val |
| | H19 Leu |

Note that first shell residues are those residues in close or direct contact with the heme iron atom and/or the bound ligand, while second shell residues are those amino acids which are not in direct contact with the heme or the bound ligand but that interact directly with first shell residues. The invention also relates to mutant hemoglobins containing mutations in any of the residues noted above, as well as double, triple and higher multiple mutations.

As noted above, the protein and DNA sequences of naturally occurring human hemoglobin are known. The present inventors have recognized and identified the mechanism by which not only ligand binding but also susceptibility to oxidation can be modulated by alteration of the residues at the heme pocket. The inventors have particularly identified the regions of the hemoglobin molecule that lead to reduced autooxidation and/or altered ligand binding properties. Moreover, the present inventors have discovered that certain mutations in the region of the heme pocket of hemoglobin result in selective increases or decreases in the affinity of one ligand without a concomittant change in the affinity of other ligands. By the same token, the present inventors have discovered mutations in the same region of the heme that result in hemoglobins that are less susceptible to autooxidation but that nonetheless retain oxygen ligand binding properties that would allow their use as oxygen carriers.

Hemoglobin mutants with high affinities for carbon monoxide and nitric oxide can be used to bind excess nitric oxide or carbon monoxide in vivo for example, in cases of carbon monoxide poisoning or in disease states characterized by excess nitric oxide. In addition, such high affinity hemoglobin mutants can be used to extract nitric oxide or carbon monoxide from cell culture or solution, or can be used to measure the rate of dissociation of these gaseous ligands from other protein molecules. Hemoglobins with low affinities for nitric oxide can be used as blood substitutes with reduced side effects due to reduced binding of nitric oxide. Mutant hemoglobins with low or no affinity for ligands can be used as inert drug delivery vehicles or in non-oxygen delivery applications of hemoglobin, such as therapeutics to enhance hematopoiesis. Hemoglobin mutants that are less susceptible to autooxidation can be used in all applications where hemoglobin can be used, for example as blood substitutes, in hemoaugmentation, and for the treatment of anemias. These more stable hemoglobin mutants can also be used as stable reagents to calibrate hemoglobin measurement instrumentation in clinical applications.

Val-E11 and His-E7 are highly conserved residues which are in Van der Waals contact with the oxygen molecule liganded to the heme iron atoms of hemoglobin; by replacing these residues the intrinsic oxygen affinity of hemoglobin can be altered. Val-E11 has been replaced with Ile, Leu, Ala, Phe and Met. The oxygen affinity of the Ala-E11 beta mutant was higher than that of naturally occurring human hemoglobin; that of the Ile-E11 beta mutant was lower. X-ray crystallographic study of the latter mutant showed that the delta-methyl group of the Ile side chain must be pushed to one side if oxygen is to bind to the iron atom. Another alteration that we have made is beta His(E7)→Phe. This mutant has an extraordinarily low oxygen affinity.

In general, mutations around the heme-$O_2$ binding site that interfere with $O_2$ binding are also desirable because of their low-affinity $O_2$ binding nature. Replacing residues that are adjacent to the face of heme that binds $O_2$ can result in lower affinity. A naturally occurring mutant Hemoglobin Bristol (beta(E11) Val→Asp) has been described with low affinity. Other mutants that are desirable are the beta Ile(E11) described herein, beta Asp(E11) and beta Glu(E11). Other residues are also in the vicinity of the $O_2$ binding site. Histidine E7 (beta $His^{63}$) can be replaced with Phe, which results in very low $O_2$ affinity. The other likely residue for mutation is beta Phe(CD1); replacement with Trp is likely to result in low $O_2$ affinity. The corresponding residues of the alpha chain may be altered instead of, or in addition to, these preferred mutations of the beta chain.

In order to increase CO affinity, His-E7 is replaced with Leu causing an apolar ligand binding site and the loss of internal water in the unliganded form. As a result, CO does not have to displace water and binds extremely tightly with an affinity that can be 30 times greater than that for His-E7 containing protein. This replacement also increases NO affinity for the same reason. However, $O_2$ affinity is greatly reduced due to the lack of stabilizing hydrogen bonding interactions. Thus, the Leu-E7 mutation can be used to engineer a hemoglobin with an extremely high affinity for CO. The resultant protein can be used to "soak" up CO from the red cells of patients with carbon monoxide poisoning and to measure the amounts of this gas generated by heme oxygenase in cell suspensions or capillaries.

Selective increases in NO and $O_2$ affinity can be achieved by replacing Leu-B10 with Phe, which displaces distal pocket water due its larger size and at the same time stabilizes both bound NO and $O_2$ by favorable electrostatic interactions with the positive edge of the phenyl ring (FIG. 5A). The resultant mutant protein shows a 6fold increase in selectivity of NO over CO and a 10-fold selectivity of $O_2$ over CO. In addition, the spontaneous and chemically induced oxidations of this mutant are inhibited due to the markedly decreased size of the ligand binding pocket. This mutation in hemoglobin can be used to measure NO levels in plasma and to elevate blood pressure by removing NO generated by NO synthase in endothelial cells.

The Leu-B10 to Trp mutation inhibits markedly the binding of all three ligands. Not only are the affinities decreased 10 to 100-fold but the rates of binding are decreased to an even greater extent The large indole side chain prevents access to the iron atom. This effect can be made even greater by incorporating large residues at the E11 position. The Trp-B10 single and double mutants interact poorly with all gases and become, in effect, inert hemoglobins and myoglobins. This allows their use as controls for measuring the effects of the proteins themselves and as vehicles for the transport of other drugs in the circulatory system without interfering with the metabolism of either NO or CO.

It has therefore been shown that the affinity of hemoglobin for gaseous ligands, particularly nitric oxide, carbon monoxide and oxygen can be altered at will by replacing residues near the ligand binding site. By adjusting ligand affinity in this way the efficiency of gas transport or gas uptake and release can be optimized to suit a specific application of the mutant recombinant hemoglobin molecule in the absence of allosteric effectors such as 2,3-DPG.

Mutations of beta residues 28 (B10), 42 (CD1), 45 (CD4), 63 (E7), 67 (E11) and 70 (E14) are of particular interest. Other beta residues of interest include 31 (1313), 44 (CD3), 66 (E10), 106 (G8) and 110 (G12). Alpha residues of interest include 29 (1310), 32 (B113), 43 (CEI), 45 (CE3), 46 (CE4), 58 (E7), 61 (E10), 62 (E11), 101 (G8) and 105 (G12).

The amino acids in the immediate vicinity of bound $O_2$ can be mutated to residues which inhibit both spontaneous and chemically induced oxidation of the iron atom and at the same time raise the partial pressure of oxygen required to achieve 50% saturation (the $P_{50}$ value). In oxyhemoglobin a chemical oxidant (for example, NO) usually first diffuses into the heme pocket and take a position in the cavity circumscribed by Val(E11), Leu(1310), Phe(CD1), and Leu or Ile(G8) after which reaction with the bound oxygen occurs. Placement of large aromatic residues at these positions should inhibit this oxidative process and thus prevents NO consumption by oxyhemoglobin. The mutations can be in either the α and β chains of recombinant hemoglobin or both the α and β chains and include but are not limited to: (1) Leu-B10→Phe or Tip; (2) Val-E11→Phe or Trp; (3) Leu or Met (B13)→Phe or Trp; (4) Leu (G8)→Phe or Trp; (5) His-E7→Gln/Val-E11→Phe; (6) His-E7→Gln/Leu-B10→Phe; (7) His-E7→Gln/Leu-B10→Phe/Val-E11→Phe; and (8) His-E7→Phe/Leu-B10→Phe/Val-E11→Phe and other multiple mutations at the primary and secondary shells of the distal pocket.

Any of the mutations of the amino acid in the hemoglobin sequence described herein can be accomplished by a number of methods that are known in the art. Mutation can occur at either the amino acid level by chemical modification of an amino acid or at the codon level by alteration of the nucleotide sequence that codes for a given amino acid. Substitution of an amino acid at any given position in a protein can be achieved by altering the codon that codes for that amino acid. This can be accomplished by site directed mutagenesis using: (1) the Amersham technique (Amersham mutagenesis kit, Amersham, Inc., Cleveland, Ohio) based on the methods of Taylor et al., Nucl. Acids Res. (1985) 13: 8749–8764; Taylor et al., (1985) Nucl. Acids Res. 13: 8764–8785; Nakamaye and Eckstein, (1986) Nucl. Acids Res. 14: 9679–9698; and Dente et al., in DNA Cloning, Glover, Ed., IRL Press (1985) pages 791–802, (2) the Promega kit (Promega Inc., Madison, Wis.) or (3) the Biorad kit (Biorad Inc., Richmond, Calif.), based on the methods of Kunkel, (1985) Proc. Natl. Acad. Sci. U.S.A. 82: 488; Kunkel et al., (1987) Meth. Enzymol. 154: 367; Kunkel, U.S. Pat. No. 4,873,192. It can also be accomplished by other commercially available or non-commercial means which incorporate the technique of site-directed mutagenesis (using mutant oligonucleotides to achieve mutagenesis).

Site directed mutagenesis can also be accomplished using PCR based mutagenesis such as that described in Zhengbin et al., pages 205–207 in PCR Methods and Applications, Cold Spring Harbor Laboratory Press, New York (1992); Jones and Howard, (1990) BioTechniques 8(2): 178; Jones and Howard, (1991) BioTechniques 10: 62–66.

Site directed mutagenesis can also be accomplished using cassette mutagenesis with techniques that are known to those of skill in the art.

Suitable pharmaceutical compositions for the mutant recombinant hemoglobins of the invention are described in co-pending application Milne, et al., Ser. No. 081339,304, filed Nov. 14, 1995 and Caspari et al., *Method for Facilitating the Use of Autologous Blood to Replace Lost Blood*, filed Jan. 13, 1995.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references cited herein are hereby incorporated by reference for their relevant teachings.

EXAMPLES

The following examples are provided by way of describing specific embodiments of the present invention without intending to limit the scope of the invention in any way.

EXAMPLE 1

Production of Mutant Recombinant Hemoglobins

A. Construction of a Bacterial System for the Production of Mutant Recombinant Hemoglobins Mutant recombinant hemoglobins were produced by fermentation of the *E. coli* strain 753 (described in co-pending application Ser. No. 08/188,374, filed Jan. 27, 1994) carrying either the plasmid pSGE0.0E4 or pSGE1.1E4. Plasmid pSGE0.0E4 codes for wild type recombinant human hemoglobin while pSGE1.1E4 codes for recombinant hemoglobin genetically linked by a glycine linker between the C terminus of a first alpha chain and the N terminus of a second alpha chain. Construction of the plasmids are described below and in U.S. Pat. No. 90/02654 and copending application Hoffman et al., U.S. Pat. No. 789,179 filed Nov. 8, 1991.

The $\alpha$L29F ($\alpha$Leu$\beta$10→Phe) mutation was constructed using oligonucleotide site-directed mutagenesis in the M13 vector phagescript according to the procedure described by Zoller and Smith (Zoller, M. J.. and Smith, M. (1987) Meth. Enz. 100: 468–500) Mutants were screened by their ability to differentially hybridize to the radiolabelled mutagenic oligonucleotide at high temperature and low salt conditions. Once the mutants were identified, mutants were then sequenced to confirm the presence of the mutation. The mutated alpha gene was then subcloned back into pSGE0.04. If the mutant alpha gene was placed into pSGE1.1E4, three subcloning steps were required:

1) Transfer of the mutant alpha gene from phagescript as an Eag1-Pst1 fragment into the Eag1-Pst1 digested desval alpha pGem vector. This step provided the mutant alpha gene with the correct 5' terminus.

2) A mutant dialpha gene with the mutations in the 3' alpha gene was constructed by inserting the Eag1 DNA fragment from dialpha pGem into the Eag1 site of the relevant mutant desval alpha pGem plasmid.

3) Finally each of the mutant dialpha genes were cloned into the pSGE1.1E4 expression vector as a Sma1-Pst1 fragment.

Transformations into DH5$\alpha$ (Hoffman et al., U.S. Pat. No. 5,545,727 issued Aug. 13, 1996) at each step in the subcloning procedure were carried out according to standard protocols (Maniatis et al. (1982) *Molecular Cloning* Cold Spring Harbor, N.Y.). The presence of the relevant mutation in the correct a gene was confirmed by sequencing at each stage in the subcloning procedure.

The $\beta$L28F ($\beta$Leu B10→Phe) mutation was made by cassette mutagenesis of the wild type $\beta$ gene. In this particular case, complementary oligonucleotides which spanned the region between the Sac II and Bg1 II sites of the $\beta$ gene were synthesized. These oligonucleotides incorporated the $\beta$L28F mutation. The mutagenesis was carried out in the pGEM1/ wild type $\beta$ plasmid and the mutant $\beta$ gene was then subcloned back into the pSGE0.0E4 vector as a Pst I-Bg1II fragment.

Mutant hemoglobins containing the Leu B10→Phe mutation in both the alpha and beta chains were constructed by replacing the wild type beta with the mutant beta gene into the subclone that already contained the alpha mutation.

B. Fermentations

Fermentor Inoculum (500 mL broth in 2 L shake flasks)

To prepare the fermentor inoculum, seed stock was thawed. Seed stock (100 ml) was grown up in 500 ml of DM1 in an Erlenmeyer flask at 37° C. in s 1 inch rotary shaker (275 to 300 rpm) for 8 to 10 hours. DM1 media is:

4.1 g/L $KH_2PO_4$
7.0 g/L $K_2HPO_4$
2.0 g/L $(NH_4)_2SO_4$
1.0 g/L $Na_3$ Citrate·$2H_2O$
153 mg/L $MgSO_4$·$7H_2O$
up to 2.30 g/L of L-proline,
2.5 mL/L of a trace metal solution containing:
    32.5 $\mu$g/ml $FeCl_3$·$6H_2O$
    1.56 $\mu$g/ml $ZnCl_2$
    2.4 $\mu$g/ml $CoCl_2$·$6H_2O$, 2.4 $\mu$g/ml $Na_2MoO_4$·$2H_2O$,
    1.22 mg/mL $CaCl_2$·$2H_2O$,
    1.54 $\mu$/ml Cu(II)$SO_4$·$5H_2O$, 0.6µg/ml H$_3$BO$_3$, 120 µl/ml HCl dissolved in purified water After sterilization of the above solution, the following components were added to achieve the final concentrations indicated:

20 mL/L 10% yeast extract/L 4.0 mL 60% glucose solution/L 0.06 mg/L of sterile-filtered 125 m thiamine HCl dissolved in purified water 0.1 mg/L of tetracycline in an ~ 50% ethanol solution Fermentor (15 L volume)

Two flasks (approximately 900 mls total volume) of fermentor inoculum was then asceptically transferred to a 15-liter BioLaffite fermentor containing approximately 6.5 liters of a solution containing:

1.83 g/L KH$_2$PO$_4$ 3.27 g/L K$_2$HPO$_4$ 1.83 g/L (NH$_4$)$_2$SO$_4$

After sterilization of the above solution, the following components were added to achieve the final concentrations indicated:

1.36 g/L Trisodium Citrate 1.36 g/L MgSO$_4$·7H$_2$0

2.87 g/L proline 3.05 g/L of the Trace Metal solution described above 0.1 mg/L tetracycline in 50% ethanol solution, 0.06 mg/L thiamine HCl in purified water, sterile filtered solution 200 g/L of 70% glucose 50+10 g/L of 30% NH$_4$OH 2 ml PPG 2000

The fermentor was ran at 30±1° C., pH 6.8, controlling dissolved oxygen at 20% and glucose between 0–6 g/L. At OD 30±2, induction was achieved by adding approximately 5.2 mL of 100 mM isopropyl thiogalactoside (IPTG) and 6 mL of 50 mg/mL hemin. At 3 hours post induction, 8.0 mL of 50 mg/mL hemin was added and at 6 hours post induction, 10 mL of 50 mg/mL hemin was added. Harvest and further purification occurs at 10 hours post induction. Other suitable fermentation conditions are described in Looker, D. et al., (1994) Meth. Enzymol. 231: 364–374.

C. Purification

Purification of expressed protein material was performed exactly as described by Looker, D. et al., (1994) Meth. Enzymol. 231: 364–374.

EXAMPLE 2

Determination of Autooxidation Rates, Rate Constants and Ligand Affinities

Association and dissociation rates for O$_2$ and CO binding to the mutants were determined using conventional laser flash photolysis and stopped-flow rapid mixing techniques as described in a detail by Rohlfs et al. (Rohlfs, R. J. et al., (1990) J. Biol. Chem. 265: 3168–3176). NO association rate constants were measured by photolyzing the NO-hemoglobin complexes at 25° C., pH 7.4 with an intense, 300 ns dye laser pulse at 578 nm (Phase-R 2100B) and following the time course for bimolecular recombination on appropriate time scales at 436 nm (Mathews, A. J. and Olson, J. S. (1994) Meth. Enzymol. 232: 363–386). NO dissociation reactions were carried out essentially as described by Moore and Gibson (Moore, E. G. and Gibson, Q. H. (1976) J. Biol. Chem. 251: 2788–2794). The mutant recombinant hemoglobin samples were prepared for determination of the NO dissociation rates by exposure of deoxygenated hemoglobin samples to NO followed by removal of excess NO by flushing the sample with nitrogen gas or by passage down a small Sephadex G-25 column equilibrated with CO-saturated sample buffer. NO dissociation was monitored in a Shimadzu UV-2101 spectrophotometer or a Hewlett-Packard HP8452 diode array spectrophotomer equipped with a temperature controlled multi-ell positioner. A concentrated, dithionite-free sample of NO-hemoglobin was injected into a sealed, 1 cm pathlength cuvette containing buffer, a bubble of pure CO, and a large excess of sodium dithionite to consume nitric oxide rapidly. The formation of the CO complex was monitored at 420–423 nm and, under these conditions, was limited by the rate of NO dissociation from the protein. The hemoglobin concentrations were 20–100 µM for the association experiments and 2–10 µM for the dissociation experiments. The buffer conditions were 0.1 M potassium phosphate, pH 7.0, 20° C. or 5 mM HEPES, 10 mM NaCl, pH 7.4, 25° C.

Equilibrium association constants for O$_2$, CO, and NO binding to R-state hemoglobin were computed as the ratios of the overall rate constants. Autooxidation rates for hemoglobin were measured using the techniques described by Brantley et al. (Brantley, R. E., et al. (1993) J. Biol. Chem. 268: 6995–7010).

EXAMPLE 3

Mutant Hemoglobins with Reduced Affinity for Nitric Oxide

Mutant recombinant hemoglobins containing Leu-B10→Phe mutations in either the alpha subunit or both the alpha and beta subunits were prepared as described in Example 1. Nitric oxide affinity was measured as described in Example 2. Only one NO association rate was observed for the photolysis of αLeu29Phe containing hemoglobins, and this corresponded to the rate observed for isolated αLeu29Phe subunits. This result suggests a large increase in the apparent quantum yield for these subunits relative to rHb0.0 and βLeu28Phe subunits. Consequently, beta subunit rate constants could not be obtained for any hemoglobin containing αLeu29Phe subunits.

The Leu B10Phe mutation caused a large 9.5-fold decrease in the alpha subunit NO association rate, but only 1.5-fold decrease in the beta subunit NO association rate, which is not a significant change in light of variation of the data (Table 2). The larger change in the alpha subunit rate due to the Leu B10Phe mutation is a reflection of the intrinsically more sterically hindered nature of the alpha subunit distal heme pocket relative to that in beta subunits. The Leu B10 Phe mutation in alpha subunits caused only a small 2.6fold increase in the rate of NO dissociation relative to rHb0.0 alpha subunits. The rate of NO dissociation from 0.0 beta subunits was not determined, but relative to human beta subunits, the rate of NO dissociation from βLeu28Phe subunits was increased 1 1.1-fold (using the average of two determinations for βLeu28Phe subunits). In terms of the association equilibrium constants, the LeuB10Phe mutation causes a 14-fold decrease in alpha subunit NO affinity, and a 4fold decrease in beta subunit NO affinity with respect to the affinities observed for R-state native hemoglobin (Table 3). The net consequence of these mutations in hemoglobin [(a0.0)(βLeu28Phe)]$_2$ is a significant decrease in NO affinity relative to that of human hemoglobin A.

A protocol similar to Example 1 was followed to prepare a mutant recombinant beta subunit except that the mutant codon coded for Trp rather than the wild type Leu. Nitric oxide affinity in these mutant beta subunits was decreased further when Leu-B10 was replaced with the even large Trp residue (Table 2). An even larger decrease in reactivity occurs for the same Trp mutation in alpha subunits. A combination of Ile-E11 and Phe or Trp-B10 mutations markedly inhibits the binding of all three gases by eliminating any available space for bound ligands.

EXAMPLE 4

Mutant Hemoglobins with Enhanced Affinity for Nitric Oxide

Mutant recombinant hemoglobins containing His-E7→Leu or His-E7→Phe mutations in either the alpha globin, the beta globin or both the alpha and beta globin are constructed as described in Example 1. Nitric oxide affinity is measured as described in Example 2. Replacing His-E7 with Leu or Phe causes large increases in NO affinity because water is already displaced from the distal pocket in the deoxy alpha and beta subunits. The Val-E11 to Leu mutation sterically displaces distal pocket water molecules and can also enhance NO binding. Combinations of these mutations, particularly the ValE11→Phe/His-E7→Leu double mutant produce hemoglobin subunits and hemoglobin tetramers with even higher NO affinities.

EXAMPLE 5

Mutant Hemoglobins with Reduced Affinity for Carbon Monoxide

Mutant recombinant hemoglobins containing Leu-B10→Phe mutations in either the alpha subunit or both the alpha and beta subunits were prepared as described in Example 1. Carbon monoxide affinity was measured as described in Example 2. The Leu-B10 to Phe mutation caused marked decreases in CO affinity 40- and 10-fold in the alpha and beta subunits, respectively (Table 3). Similar reductions in CO affinity were observed for the Leu-B10to Trp mutation. Curiously, the Leu-B10 to Ile mutation had no effect in alpha subunits but decreased the affinity of beta subunits ~ 10-fold (Table 3). Mutations at the CD3 site in beta globin had little effect on CO affinity. A variety of other Val-E11 substitutions reduce CO affinity including Phe-E11, Asn-E11, Gln-E11, and Trp-E11. Replacement of Phe-CD1 in beta subunits and Phe-CE1 in alpha subunits, particularly with Trp reduce CO affinity significantly. The largest decreases in CO affinity occur for Phe-B10/Ile-E11 and Phe-B10/Asn-E11 double mutants.

EXAMPLE 6

Mutant Hemoglobins with Enhanced Affinity for Carbon Monoxide

Mutant recombinant hemoglobins containing His-E7→Leu or Phe and/or Val-E11→Leu in either the alpha globin, the beta globin or both the alpha and beta globin are prepared as described in Example 1. Carbon monoxide affinity is measured as described in Example 2. The affinity of hemoglobin subunits for CO is enhanced by excluding distal pocket water without enhancing steric hindrance in the vicinity of the iron atom. Large increases occur when His-E7 is replaced with Leu or Phe, particularly in alpha subunits. The largest increases occur when the E7 and E11 residues are both leucines.

EXAMPLE 7

Mutant Hemoglobins with Reduced Autooxidation and Oxidation by NO

Figure 2A:
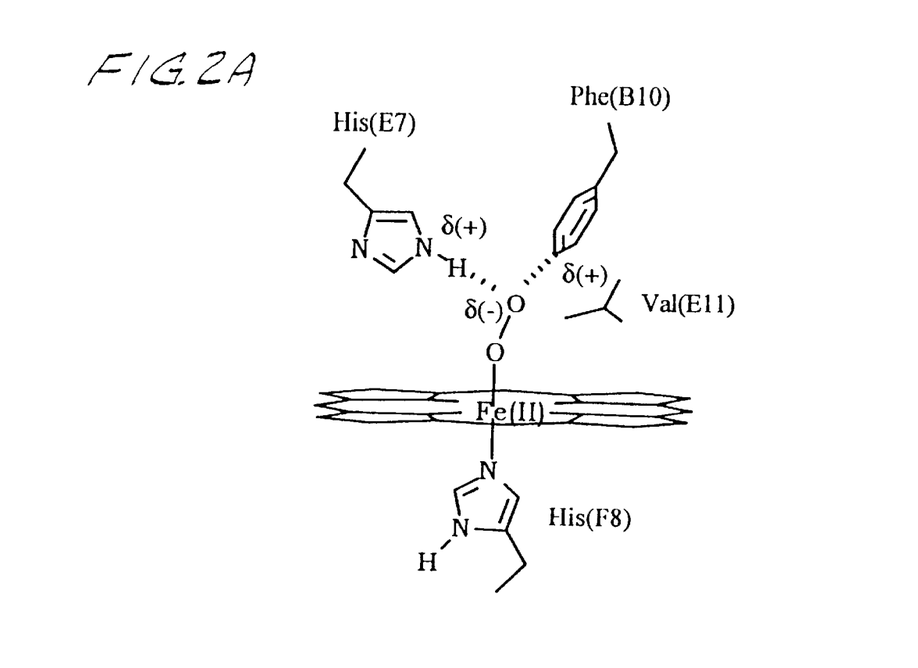
FIG. 2A shows the Leu(B10) to Phe substitution, which has high oxygen affinity and low autooxidation.
Figure 2B:
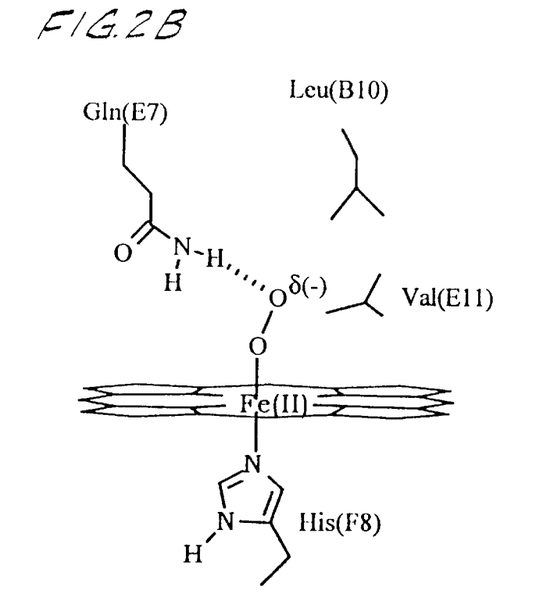
FIG. 2B shows the His(E7) to Gln mutation, which has poor oxygen affinity and high autooxidation.
Figure 2C:
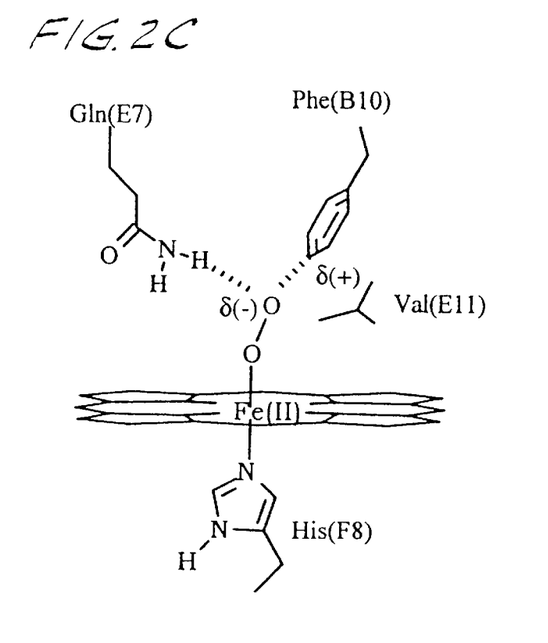
FIG. 2C shows the double mutant containing both the Leu(B10) to Phe substitution and the His(E7) to Gln mutation, which provides optimum oxygen binding and low autooxidation.

Mutant recombinant hemoglobins containing Leu-B10→Phe mutations in either the alpha subunit or both the alpha and beta subunits are prepared as described in Example 1. Mutant recombinant hemoglobins containing the mutations described below are prepared in a fashion analogous to Example 1, and autooxidation rate measurements are performed as described in Example 2. Autooxidation and NO induced oxidation rates are reduced by excluding solvents or other oxidizing or protonating agents from the distal pocket and increasing the apolar character of the distal pocket (FIGS. 1A and 1B). This is achieved by placing large aromatic residues at the B10, E11, and the B13, G8, and G12 positions in the back of the distal pocket. Phe-B10 or Phe-E11 substitutions in both hemoglobin subunits maintain low rates of oxidation while changing oxygen affinity (FIG. 2A). The Phe-B10/Phe-E11 and Phe-B10/Leu-E11 combinations reduce oxidation rates even further. His E7→Gln weakens the hydrogen bond to the bound oxygen, lowering oxygen affinity but at the same time increasing the rate of oxidation (FIG. 2B). The His E7→Gln/Leu B10→Phe double mutant shows optimum oxygen binding with low autooxidation and oxidation by NO (FIG. 2C).

TABLE 1

AMINO ACID SEQUENCE AND HELICAL RESIDUE NOTATION FOR HUMAN HEMOGLOBIN Ao

| Helix | α | Helix | β |
|---|---|---|---|
| NA1 | 1 Val | NA1 | 1 Val |
|  |  | NA2 | 2 His |
| NA2 | 2 Leu | NA3 | 3 Leu |
| A1 | 3 Ser | A1 | 4 Thr |
| A2 | 4 Pro | A2 | 5 pro |
| A3 | 5 Ala | A3 | 6 Glu |
| A4 | 6 Asp | A4 | 7 Glu |
| A5 | 7 Lys | A5 | 8 Lys |
| A6 | 8 Thr | A6 | 9 Ser |
| A7 | 9 Asn | A7 | 10 Ala |
| A8 | 10 Val | A8 | 11 Val |
| A9 | 11 Lys | A9 | 12 Thr |
| A10 | 12 Ala | A10 | 13 Ala |
| A11 | 13 Ala | A11 | 14 Leu |
| A12 | 14 Trp | A12 | 15 Trp |
| A13 | 15 Gly | A13 | 16 Gly |
| A14 | 16 Lys | A14 | 17 Lys |
| A15 | 17 Val | A15 | 18 Val |
| A16 | 18 Gly |  |  |
| AB1 | 19 Ala |  |  |
| B1 | 20 His | B1 | 19 Asn |
| B2 | 21 Ala | B2 | 20 Val |
| B3 | 22 Gly | B3 | 21 Asp |
| B4 | 23 Glu | B4 | 22 Glu |
| B5 | 24 Tyr | B5 | 23 Val |
| B6 | 25 Gly | B6 | 24 Gly |
| B7 | 26 Ala | B7 | 25 Gly |
| B8 | 27 Glu | B8 | 26 Glu |
| B9 | 28 Ala | B9 | 27 Ala |
| B10 | 29 Leu | B10 | 28 Leu |
| B11 | 30 Glu | B11 | 29 Gly |
| B12 | 31 Arg | B12 | 30 Arg |
| B13 | 32 Met | B13 | 31 Leu |
| B14 | 33 Phe | B14 | 32 Leu |
| B15 | 34 Leu | B15 | 33 Val |
| B16 | 35 Ser | B16 | 34 Val |
| C1 | 36 Phe | C1 | 35 Tyr |
| C2 | 37 Pro | C2 | 36 Pro |
| C3 | 38 Thr | C3 | 37 Trp |
| C4 | 39 Thr | C4 | 38 Thr |

TABLE 1-continued

AMINO ACID SEQUENCE AND HELICAL RESIDUE NOTATION FOR HUMAN HEMOGLOBIN Ao

| Helix | α | Helix | β |
|---|---|---|---|
| C5 | 40 Lys | C5 | 39 Gln |
| C6 | 41 Thr | C6 | 40 Arg |
| C7 | 42 Tyr | C7 | 41 Phe |
| CE1 | 43 Phe | CD1 | 42 Phe |
| CE2 | 44 Pro | CD2 | 43 Glu |
| CE3 | 45 His | CD3 | 44 Ser |
| CE4 | 46 Phe | CD4 | 45 Phe |
|  |  | CD5 | 46 Gly |
| CE5 | 47 Asp | CD6 | 47 Asp |
| CE6 | 48 Leu | CD7 | 48 Leu |
| CE7 | 49 Ser | CD8 | 49 Ser |
| CE8 | 50 His | D1 | 50 Thr |
|  |  | D2 | 51 Pro |
|  |  | D3 | 52 Asp |
|  |  | D4 | 53 Ala |
|  |  | D5 | 54 Val |
|  |  | D6 | 55 Met |
| CE9 | 51 Gly | D7 | 56 Gly |
| E1 | 52 Ser | E1 | 57 Asn |
| E2 | 53 Ala | E2 | 58 Pro |
| E3 | 54 Gln | E3 | 59 Lys |
| E4 | 55 Val | E4 | 60 Val |
| E5 | 56 Lys | E5 | 61 Lys |
| E6 | 57 Gly | E6 | 62 Ala |
| E7 | 58 His | E7 | 63 His |
| E8 | 59 Gly | E8 | 64 Gly |
| E9 | 60 Lys | E9 | 65 Lys |
| E10 | 61 Lys | E10 | 66 Lys |
| E11 | 62 Val | E11 | 67 Val |
| E12 | 63 Ala | E12 | 68 Leu |
| E13 | 64 Asp | E13 | 69 Gly |
| E14 | 65 Ala | E14 | 70 Ala |
| E15 | 66 Leu | E15 | 71 Phe |
| E16 | 67 Thr | E16 | 72 Ser |
| E17 | 68 Asn | E17 | 73 Asp |
| E18 | 69 Ala | E18 | 74 Gly |
| E19 | 70 Val | E19 | 75 Leu |
| E20 | 71 Ala | E20 | 76 Ala |
| EF1 | 72 His | EF1 | 77 His |
| EF2 | 73 Val | EF2 | 78 Leu |
| EF3 | 74 Asp | EF3 | 79 Asp |
| EF4 | 75 Asp | EF4 | 80 Asn |
| EF5 | 76 Met | EF5 | 81 Leu |
| EF6 | 77 Pro | EF6 | 82 Lys |
| EF7 | 78 Asn | EF7 | 83 Gly |
| EF8 | 79 Ala | EF8 | 84 Thr |
| F1 | 80 Leu | F1 | 85 Phe |
| F2 | 81 Ser | F2 | 86 Ala |
| F3 | 82 Ala | F3 | 87 Thr |
| F4 | 83 Leu | F4 | 88 Leu |
| F5 | 84 Ser | F5 | 89 Ser |
| F6 | 85 Asp | F6 | 90 Glu |
| F7 | 86 Leu | F7 | 91 Leu |
| F8 | 87 His | F8 | 92 His |
| F9 | 88 Ala | F9 | 93 Cys |
| FG1 | 89 His | FG1 | 94 Asp |
| FG2 | 90 Lys | FG2 | 95 Lys |
| FG3 | 91 Leu | FG3 | 96 Leu |
| FG4 | 92 Arg | FG4 | 97 His |
| FG5 | 93 Val | FG5 | 98 Val |
| G1 | 94 Asp | G1 | 99 Asp |
| G2 | 95 Pro | G2 | 100 Pro |
| G3 | 96 Val | G3 | 101 Glu |
| G4 | 97 Asn | G4 | 102 Asn |
| G5 | 98 Phe | G5 | 103 Phe |
| G6 | 99 Lys | G6 | 104 Arg |
| G7 | 100 Leu | G7 | 105 Leu |
| G8 | 101 Leu | G8 | 106 Leu |
| G9 | 102 Ser | G9 | 107 Gly |
| G10 | 103 His | G10 | 108 Asn |
| G11 | 104 Cys | G11 | 109 Val |
| G12 | 105 Leu | G12 | 110 Leu |
| G13 | 106 Leu | G13 | 111 Val |
| G14 | 107 Val | G14 | 112 Cys |
| G15 | 108 Thr | G15 | 113 Val |
| G16 | 109 Leu | G16 | 114 Leu |
| G17 | 110 Ala | G17 | 115 Ala |
| G18 | 111 Ala | G18 | 116 His |
| G19 | 112 His | G19 | 117 His |
| GH1 | 113 Leu | GH1 | 118 Phe |
| GH2 | 114 Pro | GH2 | 119 Gly |
| GH3 | 115 Ala | GH2 | 120 Lys |
| GH4 | 116 Glu | GH4 | 121 Glu |
| GH5 | 117 Phe | GH5 | 122 Phe |
| H1 | 118 Thr | H1 | 123 Thr |
| H2 | 119 Pro | H2 | 124 Pro |
| H3 | 120 Ala | H3 | 125 Pro |
| H4 | 121 Val | H4 | 126 Val |
| H5 | 122 His | H5 | 127 Gln |
| H6 | 123 Ala | H6 | 128 Ala |
| H7 | 124 Ser | H7 | 129 Ala |
| H8 | 125 Leu | H8 | 130 Tyr |
| H9 | 126 Asp | H9 | 131 Gln |
| H10 | 127 Lys | H10 | 132 Lys |
| H11 | 128 Phe | H11 | 133 Val |
| H12 | 129 Leu | H12 | 134 Val |
| H13 | 130 Ala | H13 | 135 Ala |
| H14 | 131 Ser | H14 | 136 Gly |
| H15 | 132 Val | H15 | 137 Val |
| H16 | 133 Ser | H16 | 138 Ala |
| H17 | 134 Thr | H17 | 139 Asn |
| H18 | 135 Val | H18 | 140 Ala |
| H19 | 136 Leu | H19 | 141 Leu |
| H20 | 137 Thr | H20 | 142 Ala |
| H21 | 138 Ser | H21 | 143 His |
| HC1 | 139 Lys | HC1 | 144 Lys |
| HC2 | 140 Tyr | HC2 | 145 Tyr |
| HC3 | 141 Arg | HC3 | 146 His |

TABLE 2

Effects of distal pocket mutations on NO binding to isolated α and β subunits and α and β subunits within R-state recombinant hemoglobins at pH 7.4, 25° C.

| Protein | $k'_{NO}$ $\mu M^{-1} s^{-1}$ | | $k_{NO}$ $s^{-1}$ | | $K_{NO}$ $nM^{-1}$ | |
|---|---|---|---|---|---|---|
|  | α | β | α | β | α | β |
| Native hemoglobin A | 16 | 34 | 0.000028 | 0.00005 | 570 | 590 |
| Native isolated α subunits | 29 |  |  |  |  |  |
| Native isolated β subunits |  | 110 |  |  |  |  |
| rHb0.0 | 36 | 140 |  |  |  |  |
| α 0.0 isolated | 34 |  |  |  |  |  |
| β 0.0 isolated |  | 120 |  |  |  |  |
| [(αLeu29 -> Phe/ 0.0 beta subunit)]$_2$ | 3.6 | N/A |  |  |  |  |
| [(0.0 alpha subunit/ βLeu 28 -> Phe)]$_2$ | 36 | 95 | 0.00003 | 0.00058 | 970 | 160 |
| [(αLeu -29 -> Phe/ βLeu 28 -> Phe)]$_2$ | 3.9 | N/A | 0.000098 | 0.00071 | 40 | 130 |
| αLeu 29 -> Phe, isolated | 5.5 |  |  |  |  |  |
| βLeu 28 -> Phe, isolated |  | 83 |  |  |  |  |

Note that the designation, for example, [(αLeu −29 -> Phe/βLeu 28 -> Phe)]$_2$ indicates a tetrameric hemoglobin composed of 2 alpha/beta dimers containing the indicated mutations. This notation is used throughout the table.

TABLE 3

Effects of distal pocket mutations on $O_2$ and CO binding to α and β subunits within R-state recombinant hemoglobins at pH 7, 20° C.

| Protein | $k'_{O2}$ $\mu M^{-1}s^{-1}$ | $k_{O2}$ $s^{-1}$ | $K_{O2}$ $\mu M^{-1}$ | $K_{CO}$ $\mu M^{-1}$ |
|---|---|---|---|---|
| α (0.0) | 19 | 15 | 1.3 | 300 |
| α (Leu B10 –> Ile) | 6.0 | 6.9 | 0.9 | 200 |
| α (Leu B10 –> Phe) | 0.9[a] | 0.3[a] | 3[a] | 7[a] |
| β (0.0) | 74 | 47 | 1.6 | 400 |
| β (Leu B10 –> Ile) | 27 | 4.6 | 6 | 40 |
| β (Leu B10 –> Phe) | 8[a] | 12[a] | 0.7[a] | 30[a] |
| β (Leu B10 –> Trp) | 0.016 | 0.50 | 0.03 | 40 |
| β (Ser CD3 –> His) | 92 | 24 | 4 | 500 |
| β (Ser CD3 –> Lys) | 76 | 29 | 3 | 300 |
| β (Ser CD3 –> Arg) | 87 | 30 | 3 | 300 |

$k'_{O2}$ = is the association rate constant for the reaction of oxygen with R-state hemoglobin
$k_{O2}$ = is the dissociation rate constant for the dissociation of oxygen from R-state hemoglobin
$K_{O2}$ = is the association equilibrium constant (affinity) for the binding of oxygen to R-state hemoglobin, calculated as the ratio of $k'_{O2}$ to $k_{O2}$.
$K_{CO}$ = is the association equilibrium constant (affinity) for the binding of carbon monoxide to R-state hemoglobin.
0.0 refers to hemoglobin expressed in the pSGE0.0E4 plasmid and is described above.
[a]The conditions for the Phe-B10 mutant experiments were pH 7.4, 25° C.

We claim:

1. An isolated DNA sequence encoding a mutant recombinant globin protein of a hemoglobin molecule comprising a recombinant globin with one or more mutations of any amino acid of a heme pocket of said recombinant globin, wherein said mutation is not B10(Leu→Gln) or CD3 (Ser→Arg) of the β-globin chain.

2. The DNA sequence of claim 1, wherein the mutant recombinant hemoglobin mutations occur within 4 Å of a heme moiety bound within said heme pocket.

3. The DNA sequence of claim 1, wherein the mutant recombinant hemoglobin mutations occur in that portion of said heme pocket that is a distal heme pocket.

4. The DNA sequence of claim 1, wherein the mutant recombinant hemoglobin has lower autooxidation rates than autooxidation rates measured for naturally occurring purified human hemoglobin under comparable conditions.

5. The DNA sequence of claim 1, wherein the mutant recombinant hemoglobin has either higher nitric oxide affinity than nitric oxide affinity measured for naturally occurring purified human hemoglobin under comparable conditions or has a lower rate of oxidation by NO than NO oxidation rate measured for naturally occurring purified human hemoglobin under comparable conditions.

6. The DNA sequence of claim 1, wherein the mutant recombinant hemoglobin has lower nitric oxide affinity than nitric oxide affinity measured for naturally occurring purified human hemoglobin under comparable conditions.

7. The DNA sequence of claim 1, wherein the mutant recombinant hemoglobin has lower carbon monoxide affinity than carbon monoxide affinity measured for naturally occurring purified human hemoglobin under comparable conditions.

8. The DNA sequence of claim 1, wherein the mutant recombinant hemoglobin has higher carbon monoxide affinity than carbon monoxide affinity measured for naturally occurring purified human hemoglobin under comparable conditions.

9. The DNA sequence of claim 1, wherein the mutant recombinant hemoglobin has one or more amino acid mutations selected from the group consisting of B10Leu, B13 Met, CE1 Phe, CE3 His, E7 His, CE4 Phe, E11 Val, E10 Lys, G8 Leu, E14 Ala, G12 Leu, F8 His, C7 Tyr, F4 Leu, F7 Leu, FG3 Leu, FG5 Val, G4 Asn, G5 Phe, H15 Val and H19 Leu for alpha globin and B10 Leu, B13 Leu, CD1 Phe, CD3 Ser, E7 His, CD4 Phe, E11 Val, E10 Lys, G8 Leu, E14 Ala, G12 Leu, F8 His, C7 Phe, F4 Leu, F7 Leu, FG3 Leu, FG5 Val, G4 Asn, G5 Phe, H15 Val and H19 Leu for beta globin.

10. A mutant recombinant hemoglobin has one or more amino acid mutations selected from the group consisting of B10Leu, B13 Met, CE1 Phe, CE3 His, E7 His, CE4 Phe, E11 Val, E10 Lys, G8 Leu, E14 Ala, and G12 Leu for alpha globin and B10 Leu, B13 Leu, CD1 Phe, CD3 Ser, E7 His, CD4 Phe, E11 Val, E10 Lys, G8 Leu, and E14 Ala for beta globin.

11. A mutant recombinant hemoglobin has one or more of the mutations selected from the group consisting of Leu-B10→Phe, Val-E11→Phe and His-E7→Gln for alpha and/or beta globin.

12. A mutant recombinant hemoglobin has one or more of the mutations selected from the group consisting of Leu-B10→Trp, Leu-B10→Phe, Leu-B10→Val, Leu-B10→Ile, Leu-B10→Ala, His-E7→Leu, His-E7→Trp, Val-E11→Phe, and Val-E11→Trp.

13. A non-naturally occurring nucleotide sequence encoding a mutant recombinant globin protein of a hemoglobin molecule comprising a recombinant globin with one or more mutations of any amino acid of a heme pocket of said recombinant globin.

14. The nucleotide sequence of claim 13 wherein one or more of the mutant recombinant globin mutations occur within 4 Å of a heme moiety bound within said heme pocket.

15. The nucleotide sequence of claim 13 wherein one or more of the mutant recombinant globin mutations occur in that portion of said heme pocket that is a distal heme pocket.

16. The nucleotide sequence of claim 13 wherein said mutant recombinant hemoglobin has lower autooxidation rates than autooxidation rates measured for naturally occurring purified human hemoglobin under comparable conditions.

17. The nucleotide sequence of claim 13 wherein said mutant recombinant hemoglobin has either higher nitric oxide affinity than nitric oxide affinity measured for naturally occurring purified human hemoglobin under comparable conditions or has a lower rate of oxidation by NO than NO oxidation rate measured for naturally occurring purified human hemoglobin under comparable conditions.

18. The nucleotide sequence of claim 13 wherein said mutant recombinant hemoglobin has lower nitric oxide affinity than nitric oxide affinity measured for naturally occurring purified human hemoglobin under comparable conditions.

19. The nucleotide sequence of claim 13 wherein said mutant recombinant hemoglobin has lower carbon monoxide affinity than carbon monoxide affinity measured for naturally occurring purified human hemoglobin under comparable conditions.

20. The nucleotide sequence of claim 13 wherein said mutant recombinant hemoglobin has higher carbon monoxide affinity than carbon monoxide affinity measured for naturally occurring purified human hemoglobin under comparable conditions.

21. The nucleotide sequence of claim 13 wherein the mutant recombinant globin has one or more amino acid mutations selected from the group consisting of B10Leu, B13 Met, CE1 Phe, Ce3 His, E7 his, CE4 Phe, E11 Val, E10 Lys, G8 Leu, E14 Ala, G12 Leu, F8 His, C7 Tyr, F4 Leu, F7 Leu, FG3 Leu, FG5 Val, G4 Asn, G5 Phe, H15 Val and H19 Leu for alpha globin and B10 Leu, B13 Leu, Cd1 Phe, CD3 Ser, E7 His, CD4 Phe, E11 Val, E10 Lys, G8 Leu, E14 Ala, G12 Leu, F8 His, C7 Phe, F4 Leu, F7 Leu, FG3 Leu, FG5 Val, G4 Asn, G5 Phe, H15 Val and H19 Leu for beta globin.

22. The nucleotide sequence of claim 21 wherein the mutant recombinant globin has one or more amino acid mutations selected from the group consisting of B10Leu, B13 Met, CE1 Phe, CE3 His, E7 His, CE4 Phe, E11 Val, E10 Lys, G8 Leu, E14 Ala, and G12 Leu for alpha globin and B10Leu, B13 Leu, CD1 Phe, CD3 Ser, E7 His, CD4 Phe, E11 Val, E10 Lys, G8 Leu, E14 Ala, and G12 Leu for beta globin.

23. The nucleotide sequence of claim 13 wherein the mutant recombinant globin has one or more mutations selected from the group consisting of Leu-B10→Phe, Val-E11→Phe and His-E7→Gln for alpha and/or beta globin.

24. The nucleotide sequence of claim 13 wherein the mutant recombinant globin has one or more mutations selected from the group consisting of Leu-B10→Trp, LeuB10→Phe, Leu-B10→Val, Leu-B10→Ile, Leu-B10→Ala, His-E7→Leu, His-E7→Trp, Val-E11→Phe, and Val-E11→Trp.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 141
      (B) TYPE: amino acid
      (D) TOPOLOGY: linear    (ii) MOLECULE TYPE: protein    (xi) SEQUENCE DESCRIPTION: SEQ ID NO:1:

```
Val Leu Ser Pro Ala Asp Lys Thr Asn Val Lys Ala Ala Trp Gly
                  5                  10                  15

Lys Val Gly Ala His Ala Gly Glu Tyr Gly Ala Glu Ala Leu Glu
                 20                  25                  30

Arg Met Phe Leu Ser Phe Pro Thr Thr Lys Thr Tyr Phe Pro His
                 35                  40                  45

Phe Asp Leu Ser His Gly Ser Ala Gln Val Lys Gly His Gly Lys
                 50                  55                  60

Lys Val Ala Asp Ala Leu Thr Asn Ala Val Ala His Val Asp Asp
                 65                  70                  75

Met Pro Asn Ala Leu Ser Ala Leu Ser Asp Leu His Ala His Lys
                 80                  85                  90

Leu Arg Val Asp Pro Val Asn Phe Lys Leu Leu Ser His Cys Leu
                 95                 100                 105

Leu Val Thr Leu Ala Ala His Leu Pro Ala Glu Phe Thr Pro Ala
                110                 115                 120

Val His Ala Ser Leu Asp Lys Phe Leu Ala Ser Val Ser Thr Val
                125                 130                 135

Leu Thr Ser Lys Tyr Arg
                140
```

(2) INFORMATION FOR SEQ ID NO:2:

(i) SEQUENCE CHARACTERISTICS:
        (A) LENGTH: 146
        (B) TYPE: amino acid
        (D) TOPOLOGY: unknown to applicant     (ii) MOLECULE TYPE: protein     (iii) HYPOTHETICAL: no     (xi) SEQUENCE DESCRIPTION: SEQ ID NO:2:

```
Val His Leu Thr Pro Glu Glu Lys Ser Ala Val Thr Ala Leu Trp
              5                  10                  15

Gly Lys Val Asn Val Asp Glu Val Gly Gly Glu Ala Leu Gly Arg
             20                  25                  30

Leu Leu Val Val Tyr Pro Trp Thr Gln Arg Phe Phe Glu Ser Phe
             35                  40                  45

Gly Asp Leu Ser Thr Pro Asp Ala Val Met Gly Asn Pro Lys Val
             50                  55                  60

Lys Ala His Gly Lys Lys Val Leu Gly Ala Phe Ser Asp Gly Leu
             65                  70                  75

Ala His Leu Asp Asn Leu Lys Gly Thr Phe Ala Thr Leu Ser Glu
             80                  85                  90

Leu His Cys Asp Lys Leu His Val Asp Pro Glu Asn Phe Arg Leu
             95                 100                 105

Leu Gly Asn Val Leu Val Cys Val Leu Ala His His Phe Gly Lys
            110                 115                 120

Glu Phe Thr Pro Pro Val Gln Ala Ala Tyr Gln Lys Val Val Ala
            125                 130                 135

Gly Val Ala Asn Ala Leu Ala His Lys Tyr His
            140                 145
```

(2) INFORMATION FOR SEQ ID NO:3:

(i) SEQUENCE CHARACTERISTICS:
        (A) LENGTH: 423
        (B) TYPE: nucleic acid
        (C) STRANDEDNESS: single
        (D) TOPOLOGY: unknown to applicant     (ii) MOLECULE TYPE: Other nucleic acid
        (A) DESCRIPTION: Human alpha globin sequence     (iii) HYPOTHETICAL: no     (xi) SEQUENCE DESCRIPTION: SEQ ID NO:3:

```
GTGCTGTCTC CTGCCGACAA GACCAACGTC AAGGCCGCCT GGGGCAAGGT            50

TGGCGCGCAC GCTGGCGAGT ATGGTGCGGA GGCCCTGGAG AGGATGTTCC           100

TGTCCTTCCC CACCACCAAG ACCTACTTCC CGCACTTCGA CCTGAGCCAC           150

GGCTCTGCCC AGGTTAAGGG CCACGGCAAG AAGGTGGCCG ACGCGCTGAC           200

CAACGCCGTG GCGCACGTGG ACGACATGCC CAACGCGCTG TCCGCCCTGA           250

GCGACCTGCA CGCGCACAAG CTTCGGGTGG ACCCGGTCAA CTTCAAGCTC           300

CTAAGCCACT GCCTGCTGGT GACCCTGGCC GCCCACCTCC CCGCCGAGTT           350

CACCCCTGCG GTGCACGCCT CCCTGGACAA GTTCCTGGCT TCTGTGAGCA           400

CCGTGCTGAC CTCCAAATAC CGT                                        423
```

-continued (2) INFORMATION FOR SEQ ID NO:4:

(i) SEQUENCE CHARACTERISTICS:
      (A) LENGTH: 438
      (B) TYPE: nucleic acid
      (C) STRANDEDNESS: single
      (D) TOPOLOGY: unknown to applicant    (ii) MOLECULE TYPE: Other nucleic acid
      (A) DESCRIPTION: Human beta globin sequence    (iii) HYPOTHETICAL: no    (xi) SEQUENCE DESCRIPTION: SEQ ID NO:4:

```
GTGCACCTGA CTCCTGAGGA GAAGTCTGCC GTTACTGCCC TGTGGGGCAA          50

GGTGAACGTG GATGAAGTTG GTGGTGAGGC CCTGGGCAGG CTGCTGGTGG         100

TCTACCCTTG GACCCAGAGG TTCTTTGAGT CCTTTGGGGA TCTGTCCACT         150

CCTGATGCTG TTATGGGCAA CCCTAAGGTG AAGGCTCATG GCAAGAAAGT         200

GCTCGGTGCC TTTAGTGATG GCCTGGCTCA CCTGGACAAC CTCAAGGGCA         250

CCTTTGCCAC ACTGAGTGAG CTGCACTGTG ACAAGCTGCA CGTGGATCCT         300

GAGAACTTCA GGCTCCTGGG CAACGTGCTG GTCTGTGTGC TGGCCCATCA         350

CTTTGGCAAA GAATTCACCC CACCAGTGCA GGCTGCCTAT CAGAAAGTGG         400

TGGCTGGTGT GGCTAATGCC CTGGCCCACA AGTATCAC                      438
```